United States Patent [19]

Isenberg

[11] 4,226,692
[45] Oct. 7, 1980

[54] SOLID STATE COMBUSTION SENSOR

[76] Inventor: Arnold O. Isenberg, 327 Woodside Rd., Pittsburgh, Pa. 15221

[21] Appl. No.: 908,243

[22] Filed: May 22, 1978

[51] Int. Cl.³ .................... F02D 33/00; G01N 27/58
[52] U.S. Cl. ................... 204/195 S; 60/276; 123/440; 123/489
[58] Field of Search ............... 204/15, 195 S; 324/33, 324/29; 60/276; 123/119 EC, 119 E, 32 EJ; 364/497

[56] References Cited

U.S. PATENT DOCUMENTS

| | | | |
|---|---|---|---|
| 3,558,280 | 1/1971 | Panson et al. | 23/254 |
| 3,607,424 | 9/1971 | Maki et al. | 204/195 S X |
| 3,835,012 | 9/1974 | Hemak | 204/195 S |
| 4,005,001 | 1/1977 | Pebler | 204/195 S |
| 4,101,403 | 7/1978 | Kita et al. | 204/195 S |

FOREIGN PATENT DOCUMENTS

| | | | |
|---|---|---|---|
| 2304464 | 8/1974 | Fed. Rep. of Germany | 204/195 S |
| 2657541 | 6/1977 | Fed. Rep. of Germany | 204/195 S |
| 325550 | 3/1972 | U.S.S.R. | 204/1 S |

*Primary Examiner*—G. L. Kaplan

[57] ABSTRACT

A solid state sensor consisting of at least two electrodes associated with a solid substrate exhibiting ionic conduction. The two electrodes are connected in an electrical circuit which facilitates measuring of peaking voltage signals generated by the sensor, the sensor being capable of generating peak electrical signals of more than a hundred millivolt while exposed to hot combustion gases resulting from air fuel mixtures changing between lean and rich fuel-air mixtures.

8 Claims, 5 Drawing Figures

SOLID STATE COMBUSTION SENSOR

BACKGROUND OF THE INVENTION

1. Field of the Invention:

The present invention relates to oxygen sensors and, especially, to solid state combustion gas sensors.

2. Description of the Prior Art:

Combustion gas sensors find rapidly increasing applications for controlling the combustion process of combustion apparatus such as internal combustion engines as the emission control requirements are becoming more severe.

It is known for example that engine efficiency is greatly improved, if the fuel to air ratio is stoichiometric. Also, the emission of nitrogen oxides (NOx) and of carbon monoxide (CO) is minimized when the oxygen-fuel mixture is about stoichiometric. Combustion control usually is achieved by mechanical means of measuring fuel and oxidant (air or oxygen) flows and adjusting them close to stoichiometric conditions. This method is quite suitable for combustion systems with fairly constant conditions (process heating) but fails or becomes increasingly complicated and expensive, when fuel and oxidant have to be adjusted accurately under highly variable conditions such as in connection with internal combustion engines.

Some sensing devices such as those described in U.S. Pat. No. 3,841,987 measure the oxygen content in the combustion gases. This is accomplished with solid electrolyte cells. These cells, in principle, are in the shape of a closed-end cell tube of stabilized zirconia ceramics, having platinum or other nobel metal electrodes on the inside and outside. The outside electrode is exposed to the combustion gases and the inside electrode is exposed to a gas including oxygen, of known partial pressure, i.e. usually air. The two electrode compartments are separated by sealing the tube type electrochemical cell into a wall, such that the outer surface of the cell tube with the outside electrode is exposed to the combustion gases at one side of the wall, whereas the inside of the cell tube with the other electrode is exposed to the reference gas (air) at the other side of the wall. This type of sensor produces a voltage, which depends on the partial pressure gradient from one to the other electrode. The Nernst equation, describes this relationship as follows:

$$E = \frac{R \cdot T}{n \cdot F} \ln \frac{pO_2 \text{ (high)}}{pO_2 \text{ (low)}}$$

where
- E = cell voltage [volt]
- R = universal gas constant;
- T = absolute temperature; [°K]
- n = number of transferred electrons per $O_2$ molecule;
- F = Faraday number;
- $pO_2$ (low) = low oxygen partial pressure on one electrode;
- $pO_2$(high) = high oxygen partial pressure on other electrode.

Sensors of this type, however, require considerable warm-up time until they are operative. Furthermore, they are heat shock sensitive and they require durable seals for reference oxygen compartments. In addition these sensors are subject to electrode contamination, for instance by carbon deposits or metal oxides, which results in an incorrect oxygen analysis.

Other combustion sensors such as described in U.S. Pat. No. 3,611,243 measure the resistance changes of conductive oxide films which change their resistance with varying oxygen activity. This requires the equilibration of the sensor material with the oxygen in the combustion gases. The equilibration rate is a function of temperature and thickness of the sensor body. To reduce sensor response time, the oxide films must be thin, but then they become quite fragile. They are also sensitive to contamination. Although these combustion sensors provide a value corresponding to the oxygen content in the gas mixture being measured, they all have a relatively slow response. Generally, however, the exact oxygen content in a combustion gas is of little interest as the mixture subjected to the combustion process ought to be close to stoichiometric. For the control of the combustion process it is much more important to know at which side of the stoichiometric point the mixture is and when the mixture is exactly stoichiometric. Therefore, it is most important to know without delay when the mixture is stoichiometric and in which direction the mixture is changing.

SUMMARY OF THE INVENTION

A rapidly responsive combustion sensor consists of a base member of an ionically conductive material, at least two electrodes disposed on the base member in spaced relationship and in intimate contact with the base member. The electrodes are sufficiently porous to permit gas molecules moving past the electrodes to reach the interface of the electrodes and the base member where they generate voltage differentials when the electrodes are exposed to gas at different sides of a transient gas zone moving past the sensor. Leads are connected to the electrodes for connection of the sensor in a control circuit arrangement utilizing the sensor signals for controlling a combustion process generating the gas stream.

I have discovered, that in combustion processes, however turbulent and fluctuating, there is spatially a quite sharply defined transient zone between gas streams carrying gases of greater or less than stoichiometric amounts of oxygen, and I have further found that such transient gas zones generate a differential voltage peak between two electrodes of said sensor when moving past the sensor. The separation of such different gas zones is, in fact, so sharp that the transition zone is measurable in millimeters and fractions thereof. A differential voltage signal is provided by the electrodes while the transient gas zone is located between the two electrodes and the electrodes are exposed to a different environment thereby generating the voltage difference. As soon as the transient zone moves past either electrode, the voltage difference disappears, so that the total signal has the shape of a peak.

BRIEF DESCRIPTION OF THE DRAWINGS

The invention will become more readily apparent from the following description of preferred embodiments thereof shown, by way of example only, in the accompanying drawings, wherein.

DESCRIPTION OF THE PREFERRED EMBODIMENT

Figure 1:
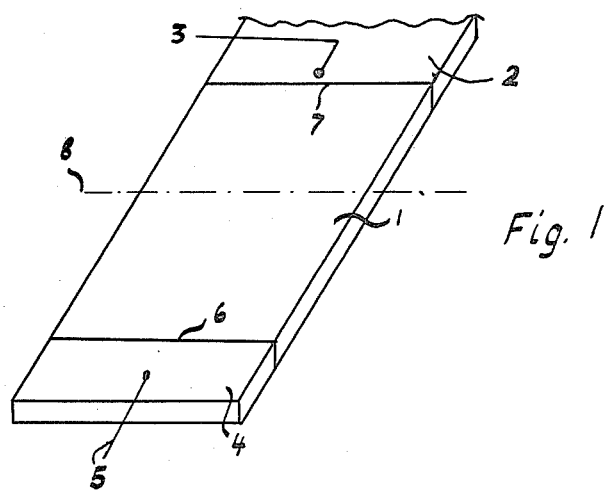
FIG. 1 shows the basic sensor structure.

FIG. 1 shows a sensor consisting of a solid member 1 of an ionically conductive material. Disposed on the outer surface of the solid member 1 and in conductive contact therewith are two electrically conductive electrodes 2 and 4. The electrodes 2 and 4 consist of layers which have electrical continuity, but are sufficiently porous to permit gas reactants to reach the interface of the electrodes 2 and 4 with the solid member 1. It is necessary that the electrode materials be suitable for operation at the elevated temperature, to which the device is subjected. Members of the platinum group of metals as well as silver and gold are suitable as electrodes, but also electronically conductive refractory materials can be used such as chromium oxide, chromium spinells, chromites with perovskite structure, also titanium oxide base electronic conductors and mixed oxides of each element of the group of lanthanides with cobalt oxide and with nickel oxide.

Figure 2:
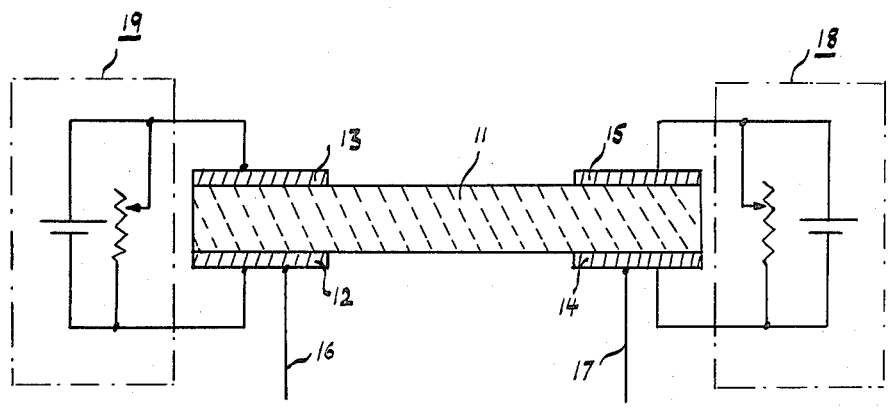
FIG. 2 shows an alternative sensor in cross-section with a D.C. electrical circuit connected to the electrodes.

Referring to FIG. 1, lead members 3 and 5 are disposed in conductive contact with each of the electrodes 2 and 4. FIG. 2 shows an alternative embodiment of the sensor of this invention, which allows the sensor to control a combustion process either on the excess oxygen (lean) side or the excess fuel (rich) side. Here, two pairs of electrodes 12, 13 and 14, 15 are disposed in intimate contact with solid member 11. Each pair of electrodes has its own DC power source 18 and 19 of variable potential.

By the application of a DC potential between a pair of electrodes 12, 13 and 14, 15 with the negative poles of the DC sources on electrodes 12 and 14, the sensor electrodes 12 and 14 can be made to assume a potential corresponding to rich conditions even when combustion gases are already marginally lean. The sensor signal, as measured between lean means 16 and 17, will be delayed until after the fuel is already stoichiometrically combusted. This means, combustion control can be achieved in the lean combustion gas region. Reversal of polarity of the DC sources on the electrode pairs, with the positive poles of each DC source on electrodes 12 and 14 will cause the electrodes 12 and 14 to assume a potential that may correspond to lean conditions before the combustion products assume that state. The sensor will then generate the signal before stoichiometric fuel combustion is achieved so that combustion control can take place in the rich combustion gas region.

Figure 3:
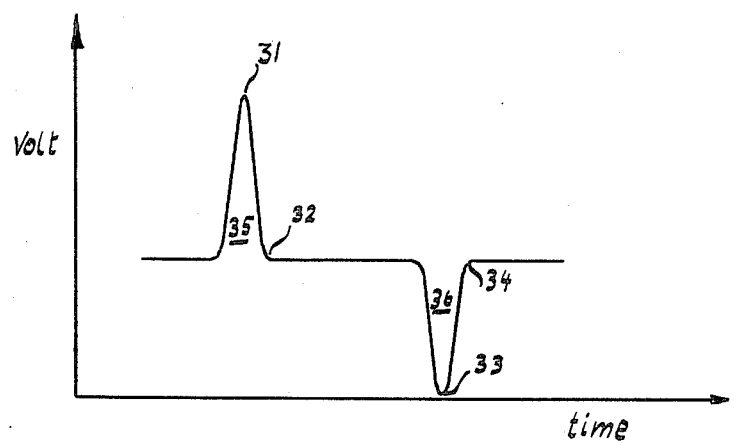
FIG. 3 shows the two types of voltage signals obtained by the sensor when a transient gas zone moves past the sensor.

Any combustion process, to whose exhaust gases a sensor as described in FIG. 1 or 2 is exposed and which fluctuates around the point of stoichiometric combustion will create sharply defined transient spatial gas zones, as discussed earlier. Referring to FIG. 1, as soon as the transient zone reaches a position between point 6 and 7, it will generate a voltage difference between electrodes 4 and 2. It is not necessary that the transient gas zone, indicated by the dashed line 8 in FIG. 1, is normal to the shortest distance line between electrode centers of the sensor; however, the highest voltage signal is achieved in this electrode orientation. After the transient gas zone has moved also past the other electrode (2), the sensor electrodes assume the same potential. A newly arriving transient gas zone of changing (reversing) oxygen activity moving in the same direction generates a voltage peak of opposite polarity. Combustion fluctuation and periodically crossing of the stoichiometric point of combustion, therefore, results in a multiple sequence of voltage peaks of opposite direction as shown and explained in connection with FIG. 3. FIG. 3 is a potential-over-time diagram. One may assume: at point 31, the electrodes sense the completed passing over the first electrode of a transient gas zone separating exhaust gas having excess oxygen on one side and excess fuel on the other side. At point 32, the voltage difference between both electrodes disappears because the zone passed also the second electrode and both electrodes are at the same potential (same oxygen activity). One may further assume that, at point 31 of peak 35, an electrical circuit triggered the cut-back of air, changing the combustion products from having excess oxygen to having excess fuel. This generates a new transient zone whose passage past the first electrode is indicated by point 33 in FIG. 3. When the transient zone has moved past the second electrode the potential difference between the two sensing electrodes disappears again (point 34). At point 33 of peak 36, the electrical circuit can trigger a means to increase the oxygen supply to the combustion thus completing one control cycle using the electrical signal generated by the sensor.

Figure 4:
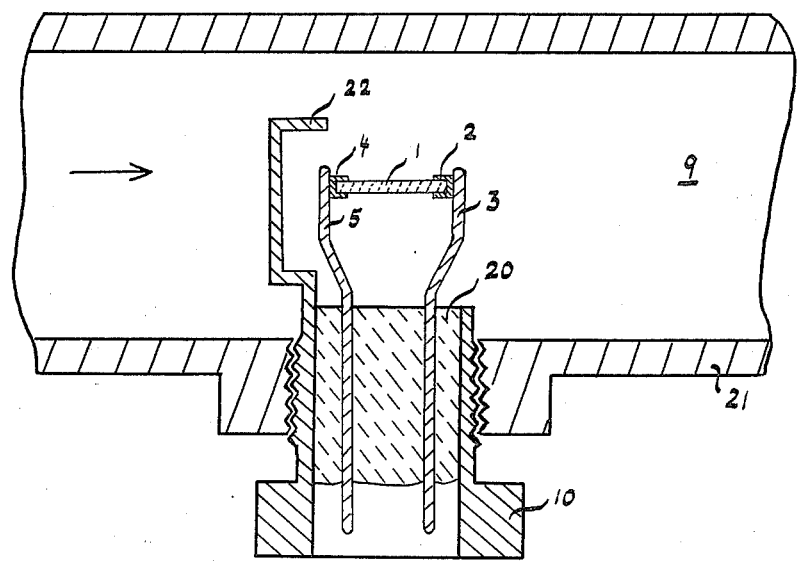
FIG. 4 shows the sensor mounted in a duct carrying a gas to be monitored.

FIG. 4 shows a sensing device 10 mounted in a gas conduit 9, where the sensor is of the type shown in FIG. 1 consisting of solid member 1 and electrodes 2 and 4. Lead members 3 and 5 serve also as mounting posts for supporting the sensor. The sensing device 10 is mounted into an opening in the wall 21 of conduit 9. The sensing device is preferably of the spark plug type, having a ceramic insulation 20 through which the lead members 3 and 5 extend.

The solid ionic conducting members which form the substrates for the electrodes can be made of various materials and can assume a wide variety of shapes. While solid oxygen ion conductive materials are preferred for solid member 1 of FIG. 1, also cation conductors, or mixed oxygen ion/cation conductors can be employed. Mixed electronic/ionic conductors can usefully be employed, as long as the sensor electrical signal is not totally suppressed by electronic shorting. Materials usable for the solid sensor member may consist of zirconia ($ZrO_2$) base materials with admixtures of oxides of alkaline earth elements, oxides of scandium, yttrium and of the lanthanide elements, in order to achieve oxygen ion conductivity in the zirconia ceramics.

The concentration of admixture of these oxides to zirconia can vary widely from one mol percent to fifty mol percent. Ceria ($CeO_2$) base ceramic sensor materials are preferred in applications where high oxygen conductivity and heat shock resistance are needed. Sintered bodies of gadolinia doped ceria are also very desirable. The gadolinia content in a mixture with ceria can vary between one mol percent and fifty mol percent, but generally is at about twenty-three mol percent. Other oxide admixtures to ceria include the same elements as used in admixtures with zirconia and in the same concentration range. Magnesium oxide (MgO) is another base oxide, that can be made ionically more conductive by co-sintering with sodium fluoride and lithium fluoride. Also, calcium fluoride ($CaF_2$) can be used at it becomes a fluorine ion conductor, when doped with oxides or fluorides of the alkaline elements. Uranium dioxide ($UO_2$) is an acceptable solid conductor of oxygen ions when mixed with oxides of the elements mentioned in connection with zirconia and in the same concentration range. Thoria ($ThO_2$) meets condutivity requirements as solid ion conducting member for sensors of this invention, when doped with oxides of elements mentioned in connection with zirconia and in the same concentration. Another possible oxide base material used in this connection is bismuth oxide ($Bi_2O_3$) doped with strontium oxide (SrO) or with calcium oxide (CaO) or with lanthanum oxide ($La_2O_3$).

$La_{1-x}Ca_xAlO_3$ (x=0 to 0.5),
$La_{1-x}Ba_xAlO_3$ (x=0 to 0.5),
$CaTi_{1-x}Mg_xO_3$ (x=0 to 0.5),
$CaTi_{1-x}Al_xO_3$ (x=0 to 0.5),
$SrTi_{1-x}Al_xO_3$ (x=0 to 0.5),
$BaTh_{1-x}La_xO_3$ (x=0 to 0.5),
$BaZr_{1-x}Bi_xO_3$ (x=0 to 0.5),
$BaCe_{1-x}Bi_xO_3$ (x=0 to 0.5), are some of the oxygen ion conductive materials acceptable for use as solid ion conducting members. Typical examples of cation conductors are $\beta$-alumina, $\beta'$-alumina, $\beta''$-alumina, $\beta$-iron oxide, which represent sodium ion conductors. Other useful cation conductors are lithium sulfate ($Li_2SO_4$) and soda-lime-glasses.

The solid conductive member 1 as shown in FIG. 1 may have various shapes. Preferred shapes are small bars of a circular, square or rectangular cross-section of about three square millimeters cross-sectional surface area. A member length of ten to fifteen millimeters is sufficient. The solid conductive members may also be in the form of tubes (closed or open). The sensor material may, for example, consist of a small rectangular bar of 15 mm length, 1 mm thickness and 3 mm width composed of an oxygen ion conductor like sintered gadolinia doped ceria. The electrodes attached to the ends of the sensor bar are platinum electrodes and cover nearly 3 mm of the sensor length around each end. Platinum wires are attached to the electrodes.

OPERATION

FIG. 3 shows the sensor signals generated by the sensor according to FIG. 1. There is a voltage peak, which is induced by the passing past the sensor of a sharp transient zone of adjacent gas phases with greatly different oxygen activities. Points 31 and 33 represent a condition in which the transient zone of changing oxygen activities is positioned between electrodes 2 and 4 of FIG. 1. Such sharp transient zones of a large oxygen activity gradient of several orders of magnitude are observed in all gaseous combustion products when combustion conditions fluctuate periodically around the point of stoichiometric admixture of fuel and oxydant that is whenever the air fuel mixture changes from rich to poor or vice versa. When combustion gases flowing in one general direction over a sensor change from having a small amount of excess fuel (rich) to having small amounts of excess oxygen (lean) and again back to a rich composition, the sensor emits two subsequent voltage peaks of opposite polarity which are depicted in FIG. 3, as they appear on the screen of an oscilloscope.

It is understood that any number of individual sensors can be used and so arranged in parallel or series electrical connection that a common signal of high strength is obtained. The voltage signal of one sensor or sensor array may also be used to produce a current signal of the same general shape as the voltage signal, that is, the sensor produces subsequent current peaks of different polarity.

Figure 5:
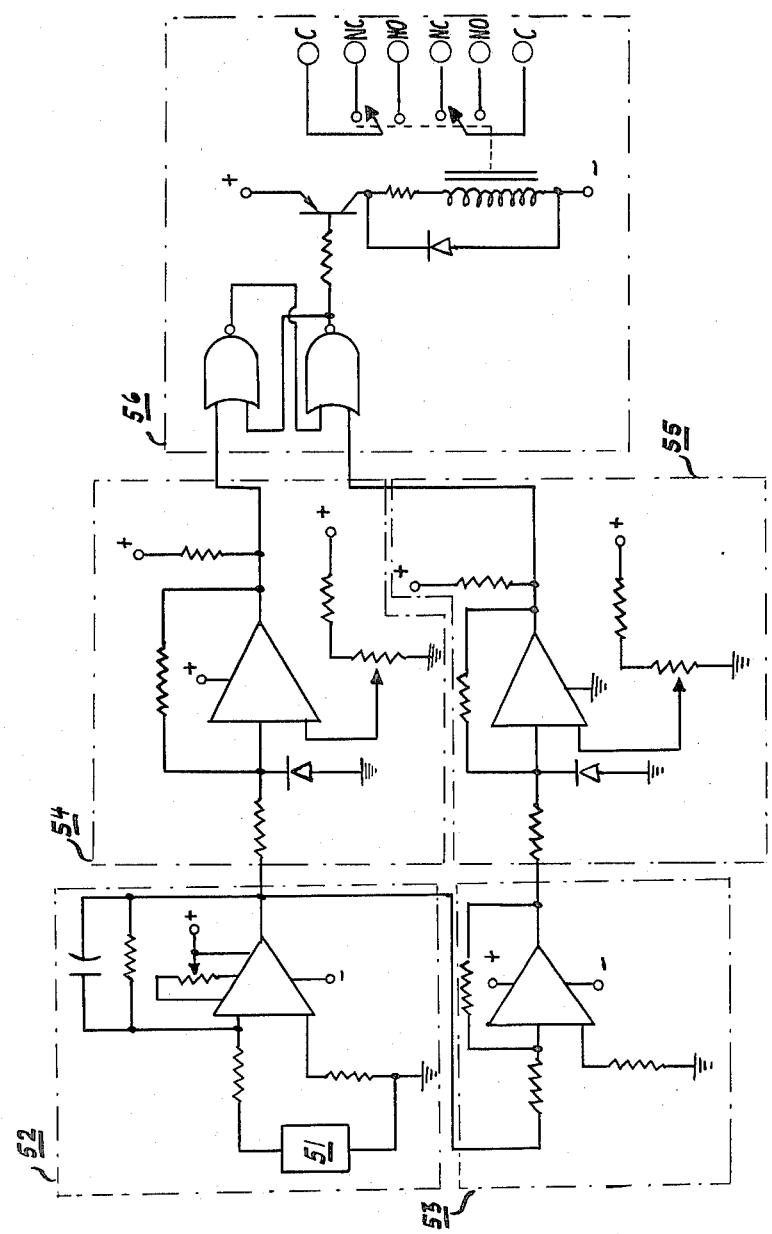
FIG. 5 shows a measuring circuit for converting the signal obtained by the sensor to a control signal for combustion process control.

FIG. 5 shows an electric circuitry arrangement for converting the voltage signal of the sensor 51 into control signal suitable for controlling a combustion process. The electrical circuitry arrangement consists of an input inverting amplifier circuit 52 with matching impedance for the sensor, having a gain of ten, and an inverting amplifier circuit 53 to invert signal coming from 52 into opposite polarity. The signal from amplifier circuit 52 is supplied to a negative pulse voltage comparator circuit 54 and the signal from circuit 53 is supplied to a positive pulse voltage comparator 55. Resulting signals from 54 and 55 enter a circuit 56 comprised of a flip-flop memory that controls the state of a relay for switching purposes.

If, during operation of an internal combustion engine, a sensor disposed in the exhaust duct of a cylinder provides for example a signal which indicates that the gas mixture burnt in the cylinder was too rich the gas mixture may be changed by the control signal derived from the sensor signal to become leaner by a predetermined amount. If then the sensor signal indicates that the gas mixture has become leaner than stoichiometric or leaner than desired the mixture will again be changed by this resulting control signal to become richer by a predetermined amount, etc. The amounts of changes may also be varied, that is the forward and backward steps may be made smaller and smaller so as to approach the desired mixture composition value.

Control of internal combustion engines by sensors, requires fast sensor response but also sensor sensitivity at temperatures of 300° C. and higher. The sensor according to my invention meets these requirements to a high degree.

The solid state sensor according to this invention finds useful application in combustion processes in order to achieve more efficient fuel utilization. Gas, oil and coal fired process heating equipment can be controlled with high accuracy with this sensor, that exhibits peak sensitivity at the ideal, stoichiometric, point of fuel combustion. The sensor's rapid response, small dimensions and structural insensitivity, however, render it especially suitable for use as an exhaust gas sensor of internal combustion engines whose fuel mixtures are fine-tuned on the basis of values obtained from exhaust gas sensing devices installed in the exhaust gas duct.

The response of the sensor is without delay. It is in fact so fast that, in a fuel injected combustion engine, which has sensors arranged in its exhaust system near the exhaust port of each cylinder, adjustments to the gas mixture supplied to a cylinder during an intake stroke may be made on the basis of a sensor signal obtained during the preceding exhaust stroke.

The present invention is, of course, not limited to the arrangements described and shown herein.

The incorporation in the sensing arrangement of a sensor element of an alternate design such as shown in FIG. 2 for example is easily accomplished by incorporating several more lead members so as to contact a multiplicity of electrodes. Although the sensors are normally sufficiently heated by the exhausted combustion gases, for instance, of an internal combustion engine, additional heating can be accomplished by auxiliary heaters associated with the sensors.

In order to protect the sensors from the high speed combustion gas flow a protective shield 22, (FIG. 4) may be arranged in front of the sensor with respect to the direction of the flow of the gas to be monitored.

Also, the electrodes may be provided with a protective coating as known in the art.

What is claimed is:

1. A combustion sensing arrangement comprising: a conduit receiving the exhaust gases of a combustion process; a unitary solid state combustion sensor arranged in said conduit and consisting of a base member of an oxygen ion conductive material; and at least two electrodes disposed on said base member in intimate contact therewith and in spaced relationship so as to provide an ion conductive path between said electrodes through said base member, said base member and said electrodes being equally exposed to said exhaust gases and said sensor being arranged in said conduit with the associated electrodes spaced in the direction of flow such that the exhaust gas flowing through the conduit reaches first one and then the other of said associated electrodes and a transient gas front having different oxygen activities at opposite side thereof is momentarily disposed between said electrodes, said electrodes having leads for connection to an electrical signal processing circuit for supplying thereto signals generated by the sensor when a transient gas front moves past the sensor.

2. A solid state combustion process control arrangement, comprising: a unitary solid state combustion sensor consisting of a base member of oxygen ion conductive material arranged in a conduit receiving exhaust gas from a combustion process, at least two electrodes disposed on said base member in spaced relationship so as to provide an ion conductive path between said electrodes through said base member, said base member and said electrodes being equally exposed to said exhaust gases and said electrodes being in intimate contact with said base member, said base member being arranged in said conduit with the associated electrodes spaced in the direction of flow such that gas flowing through the conduit reaches first one and then the other of said associated electrodes and a transient gas front having different oxygen activities at opposite side thereof is momentarily disposed between said electrodes; leads connected to said electrodes; and a control circuit connected to said sensor through said leads for converting signals received from said sensor to control signals for controlling a combustion process with which the sensor is associated, said control circuit including means for amplifying said sensor signals; means for inverting the signals; means for comparing the amplified and the inverted signals; memory means for signals received from said comparing means; and output means for providing a control signal to said combustion means.

3. A solid state combustion sensor as recited in claim 1 or 2, wherein a pair of electrodes is disposed on said base member at each of said spaced locations and means are provided for applying a biasing potential across each pair of electrodes so as to permit biasing the signal generated by said sensor toward either one of a rich and lean burning condition.

4. A solid state combustion sensor for disposition in the combustion gas stream of a combustion process, said sensor comprising: a base of an oxygen ion conductive material; at least two pairs of electrodes disposed on said base member in spaced relationship, said base member being so oriented in said gas stream that said two pairs of electrodes are disposed at locations spaced from each other in flow direction of said gas stream so as to cause gas flowing past said base member to contact first one and then the other of said pairs of electrodes whereby said one and said other of said pairs of electrodes are momentarily exposed to gas of different oxygen activities when a combustion gas front having different oxygen activities at opposite sides moves past said base member; said electrodes being in intimate contact with said base member and having leads electrically connected to said electrodes for connecting said sensor in an electrical control circuit arrangement utilizing the signal generated electronically by said sensor when arranged in a combustion gas stream of periodically varying oxygen activity, and means for applying a biasing potential across each pair of electrodes so as to permit biasing the signal generated by said sensor toward either one of a rich and lean burning condition.

5. A solid state combustion sensor as recited in claim 4, wherein said base member consists of mixed oxides on the basis of ceria ($CeO_2$) and said electrodes consists of platinum group elements.

6. A solid state combustion sensor as recited in claim 4, wherein said base member consists of mixed oxides on the basis of zirconia ($ZrO_2$) and said electrodes consist of platinum group elements.

7. A solid state combustion sensor as recited in claim 4, wherein said sensor is part of a sensing device adapted to be mounted in the wall of a conduit receiving a gas stream of varying oxygen activity, said sensing device including a body of an insulating material and said leads extending through said body of insulating material and supporting said sensor spaced from said body.

8. A solid state combustion sensor as recited in claim 4 or 7, wherein a protective shield is arranged in front of said sensor with respect to direction of the flow of the gas to be monitored.

* * * * *